(12) United States Patent
Noda et al.

(10) Patent No.: US 10,379,035 B2
(45) Date of Patent: Aug. 13, 2019

(54) APPEARANCE INSPECTION APPARATUS AND APPEARANCE INSPECTION METHOD

(71) Applicant: Panasonic Intellectual Property Management Co., Ltd., Osaka (JP)

(72) Inventors: Akihiro Noda, Nara (JP); Hiroya Kusaka, Hyogo (JP); Taro Imagawa, Osaka (JP); Shunsuke Yasugi, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 17 days.

(21) Appl. No.: 15/901,506

(22) Filed: Feb. 21, 2018

(65) Prior Publication Data

US 2018/0180534 A1 Jun. 28, 2018

Related U.S. Application Data

(63) Continuation of application No. PCT/JP2016/003698, filed on Aug. 10, 2016.

(30) Foreign Application Priority Data

Mar. 28, 2016 (JP) ................................. 2016-062995

(51) Int. Cl.
*H04N 7/18* (2006.01)
*G01N 21/27* (2006.01)
(Continued)

(52) U.S. Cl.
CPC .......... *G01N 21/27* (2013.01); *G01N 21/251* (2013.01); *G01N 21/474* (2013.01); *G01N 21/84* (2013.01);
(Continued)

(58) Field of Classification Search
CPC ............................... H04N 9/045; H04N 9/064
(Continued)

(56) References Cited

U.S. PATENT DOCUMENTS 6,271,520 B1 8/2001 Tao et al.
2009/0185182 A1 7/2009 Kim et al.

FOREIGN PATENT DOCUMENTS

JP 2-218944 8/1990
JP 4-307357 10/1992
(Continued)

OTHER PUBLICATIONS

International Search Report of PCT application No. PCT/JP2016/003698 dated Oct. 18, 2016.
(Continued)

*Primary Examiner* — Anand S Rao
(74) *Attorney, Agent, or Firm* — Wenderoth, Lind & Ponack, L.L.P.

(57) ABSTRACT

An appearance inspection apparatus includes a lighting unit, an imaging unit, a memory, an operating unit, a detecting unit, and a determination unit. The lighting unit has a plurality of light sources emitting single-wavelength light with relative spectral distributions different from one another, and substantially simultaneously irradiates a photographic subject with illumination light. The imaging unit captures light discharged by the photographic subject. The memory stores information about sensitivity characteristics of the imaging unit for each color. The operating unit separates an image into a first, a second, and a third image, for each component of the single-wavelength light, using the information. The detecting detects information about a specific area of the photographic subject using the first and the second image. The determination unit extracts an amount of
(Continued)

image characteristics corresponding to a characteristic part present in the specific area using the first and the third image.

16 Claims, 10 Drawing Sheets

(51) Int. Cl.
*G06T 7/90* (2017.01)
*G01N 21/84* (2006.01)
*G06T 7/00* (2017.01)
*H04N 5/235* (2006.01)
*G01N 21/25* (2006.01)
*G01N 21/47* (2006.01)
*H04N 5/225* (2006.01)
*H04N 5/232* (2006.01)
*H04N 9/04* (2006.01)
*H04N 9/64* (2006.01)
*G06T 7/13* (2017.01)
*G01N 33/02* (2006.01)

(52) U.S. Cl.
CPC .............. *G06T 7/0004* (2013.01); *G06T 7/90* (2017.01); *H04N 5/2256* (2013.01); *H04N 5/232* (2013.01); *H04N 5/2354* (2013.01); *H04N 9/045* (2013.01); *H04N 9/64* (2013.01); *G01N 33/02* (2013.01); *G06T 7/13* (2017.01); *G06T 2207/10016* (2013.01); *G06T 2207/10024* (2013.01); *G06T 2207/10152* (2013.01); *G06T 2207/30128* (2013.01)

(58) Field of Classification Search
USPC ...................................................... 348/89–92
See application file for complete search history.

(56) References Cited

FOREIGN PATENT DOCUMENTS

| | | |
|---|---|---|
| JP | 9-264849 | 10/1997 |
| JP | 2004-077128 | 3/2004 |
| JP | 2005-351645 | 12/2005 |
| JP | 2006-300767 | 11/2006 |
| JP | 2008-209404 | 9/2008 |
| JP | 2009-216485 | 9/2009 |
| JP | 2012-117858 | 6/2012 |
| JP | 2012-243097 | 12/2012 |
| JP | 2013-068489 | 4/2013 |
| JP | 2014-085112 | 5/2014 |

OTHER PUBLICATIONS

Katsuichi Kitagawa, "Crosstalk Compensation for Three-Wavelength Interferometry", The Society of Instrument and Control Engineers Sangyo Ronbunshu, Sep. 2009, vol. 8, No. 14, pp. 113 to 116.

APPEARANCE INSPECTION APPARATUS AND APPEARANCE INSPECTION METHOD

BACKGROUND

Technical Field

The present disclosure relates to an apparatus that inspects the appearance of a photographic subject based on an image captured by irradiating onto the subject with light and to such a method.

Description of the Related Art

Patent literature 1 discloses an appearance inspection apparatus for agricultural products. The apparatus includes an imaging means, multiple color specification units specifying a characteristic color of bruised parts, a logical OR operating unit, and a bruise detecting unit. Each color specification unit includes an image-processing unit and a logical AND operating unit. The image-processing unit applies multiple image-processing for extracting a characteristic color specified to an image obtained by imaging agricultural products by the imaging means. The logical AND operating unit performs logical AND operation on multiple images image-processed by the image-processing unit. The logical OR operating unit performs logical OR operation on an image produced by logical AND operation by the logical AND operating unit of each color specification unit. The bruise detecting unit detects bruises of an agricultural product based on the image produced by logical OR operation by the logical OR operating unit.

This operation allows bruised agricultural products to be screened more accurately.

CITATION LIST

Patent Literature

PTL 1: Japanese Patent Unexamined Publication No. 2006-300767

SUMMARY

The present disclosure provides an apparatus that performs appearance inspection for a photographic subject speedily and accurately.

An appearance inspection apparatus of the disclosure includes a lighting unit, an imaging unit, memory, an operating unit, a detecting unit, and a determination unit. The lighting unit has a plurality of light sources emitting single-wavelength light with relative spectral distributions different from one another, and substantially simultaneously irradiates a photographic subject with illumination light emitted by the plurality of light sources. The imaging unit captures light discharged by the photographic subject in response to the illumination light irradiated by the plurality of light sources. The memory stores information about sensitivity characteristics of the imaging unit for each color. The operating unit separates an image captured by the imaging unit into a plurality of single-wavelength images including a first image, a second image, and a third image, for each component of the single-wavelength light, using the information about the sensitivity characteristics of the imaging unit for each color. The detecting detects information about a specific area of the photographic subject using the first image and the second image chosen from the plurality of single-wavelength images. The determination unit extracts an amount of image characteristics corresponding to a characteristic part present in the specific area detected by the detecting unit using the first image and the third image chosen from the plurality of single-wavelength images.

An appearance inspection method of the disclosure irradiates substantially simultaneously a photographic subject with illumination light emitted by a plurality of light sources emitting single-wavelength light with relative spectral distributions different from one another. The method further generates an image by capturing light discharged by the photographic subject in response to the illumination light irradiated from the plurality of light sources. Then, the method separates the image captured into a plurality of single-wavelength images including a first image, a second image, and a third image for each component of the single wavelength using the information about sensitivity characteristics of the imaging unit for each color. Then, the method detects information about a specific area of the photographic subject using the first image and the second image chosen from the plurality of single-wavelength images. Then, the method extracts an amount of image characteristics corresponding to a characteristic part present in the specific area detected by the detecting unit using the first image and the third image chosen from the plurality of single-wavelength images.

The present disclosure provides a apparatus performing appearance inspection for a photographic subject speedily and accurately.

DETAILED DESCRIPTION OF THE PREFERRED EMBODIMENTS

Hereinafter, a detailed description is made of various embodiments with reference to the related drawings as appropriate. However, a detailed description more than necessary may be omitted, such as a description of a well-known item and a duplicate description for a substantially identical component, to avoid an unnecessarily redundant description and to allow those skilled in the art to easily understand the following description.

Note that accompanying drawings and the following descriptions are provided for those skilled in the art to well understand the disclosure, and these are not intended to limit the subjects described in the claims by the drawings and the description.

In the following descriptions, an expression such as "store an image" means "store data of an image." In the following descriptions, an observation target (a photographic subject) is assumed to be a stemmed tomato with its fruit bruised. A stemmed tomato is classified into three areas: fruit, stem, and bruise. In this disclosure, a part (e.g. a bruise) as a target of appearance inspection is defined as "a characteristic part" of a photographic subject. A part including or possibly including a characteristic part (e.g., fruit) is defined as "a specific area."

Hereinafter, a description is made of the configuration and operation of the apparatus in a case of extracting a bruise on the surface of a tomato.

0-1. Reflected Light and Spectral Distribution

Reflected light is discharged from a substance when it is irradiated with light, representing the characteristics of the substance. Accordingly, reflected light can be used for analyzing a substance qualitatively and quantitatively.

In this disclosure, the expression of "discharge light in response to light irradiated onto a substance" is also expressed as "reflect irradiated light."

A spectral distribution is obtained by a method such as separating light continuously by wavelength using a diffractive grating. A spectral distribution shows the intensity of light by wavelength. A spectral distribution of reflected light represents the characteristics of a substance irradiated with light. The shape of a graphed spectral distribution, where the horizontal axis represents wavelength and the vertical axis represents the intensity of reflected light by wavelength, represents qualitative information about the substance. The overall intensity in the graph represents qualitative information about the substance. Hereinafter, information about the shape of a spectral distribution representing the qualitative information about the substance is referred to as a relative spectral distribution.

Figure 1:
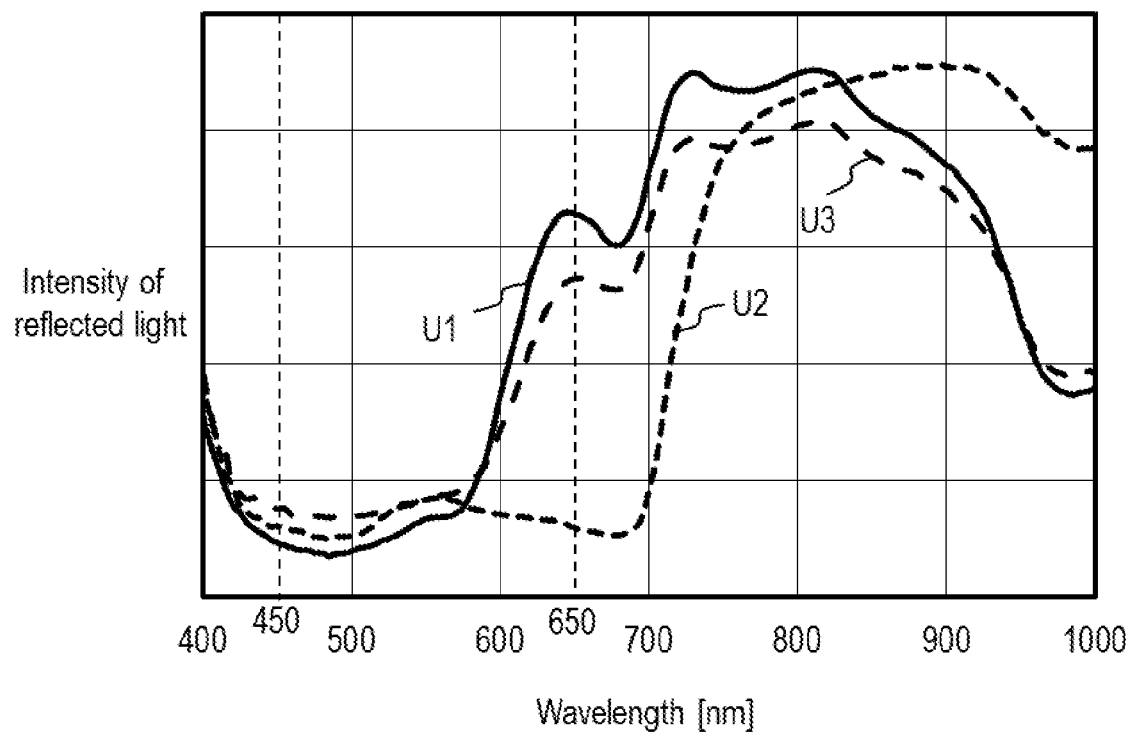
FIG. 1 illustrates an example of spectral distributions of a photographic subject.

FIG. 1 illustrates spectral distributions by the area of a tomato as an example of a photographic subject. The vertical axis represents the intensity of reflected light; the horizontal axis, wavelength (nm). Solid line U1 shows a spectral distribution of the fruit; dotted line U2, the stem; wave line U3, the bruise. As shown in FIG. 1, a tomato has spectral distributions different by part (i.e., fruit, stem, and bruise). Using the difference between areas allows detecting information about a specific area. For example, the difference of the intensity of reflected light between the fruit and the stem is largest around a wavelength of 650 nm. Hence, using the intensity of reflected light at each area around a wavelength of 650 nm allows separating the areas of the fruit and the stem of a tomato in the image produced by capturing reflected light. A narrower wavelength band of reflected light allows separating a specific area from the captured image more accurately.

0-2. RGB Vector

In this disclosure, RGB values of each pixel of an image captured by an RGB camera are regarded as a three-dimensional vector and are represented as a three-dimensional vector. Hereinafter, a description is made of the direction and length of an RGB vector.

The direction of an RGB vector refers to information reflecting the ratio of the RGB colors that includes information about the qualitative characteristics of a substance irradiated with light. In other words, the direction of an RGB vector is related to a relative spectral distribution. Examples of the direction of an RGB vector include an RGB vector with its length normalized to one. Meanwhile, the length of an RGB vector is a value representing the overall RGB intensity that includes information about the quantitative characteristics of the substance irradiated with light.

When observation light with a certain spectral distribution is captured by an RGB camera, the values of the elements of the RGB vector of a pixel in the captured image are provided by multiplying the spectral distribution of the observation light by the spectral sensitivity characteristics of bands R, G, and B; and further integrating the resulting values by each band width. Accordingly, the same relative spectral distribution of observation light results in the same direction of the RGB vector. In other words, the direction of an RGB vector includes information about a relative spectral distribution of observation light. When only the intensity of observation light changes with its relative spectral distribution remaining the same, only the length of the RGB vector changes. In other words, the length of an RGB vector includes information about the intensity of a spectral distribution of the observation light.

For example, it is assumed that vector V1 is an RGB vector of reflected light obtained by irradiating a photographic subject with light of certain intensity; vector V2 is that of twice the intensity. Then, the length of vector V2 is twice that of vector V1 while they have the same direction.

In this disclosure, it is regarded that an RGB vector is as well one spectral distribution and the direction of an RGB vector is as well one relative spectral distribution, and thus an RGB vector is also represented as a spectral distribution; the direction of an RGB vector, a relative spectral distribution.

Figure 2:
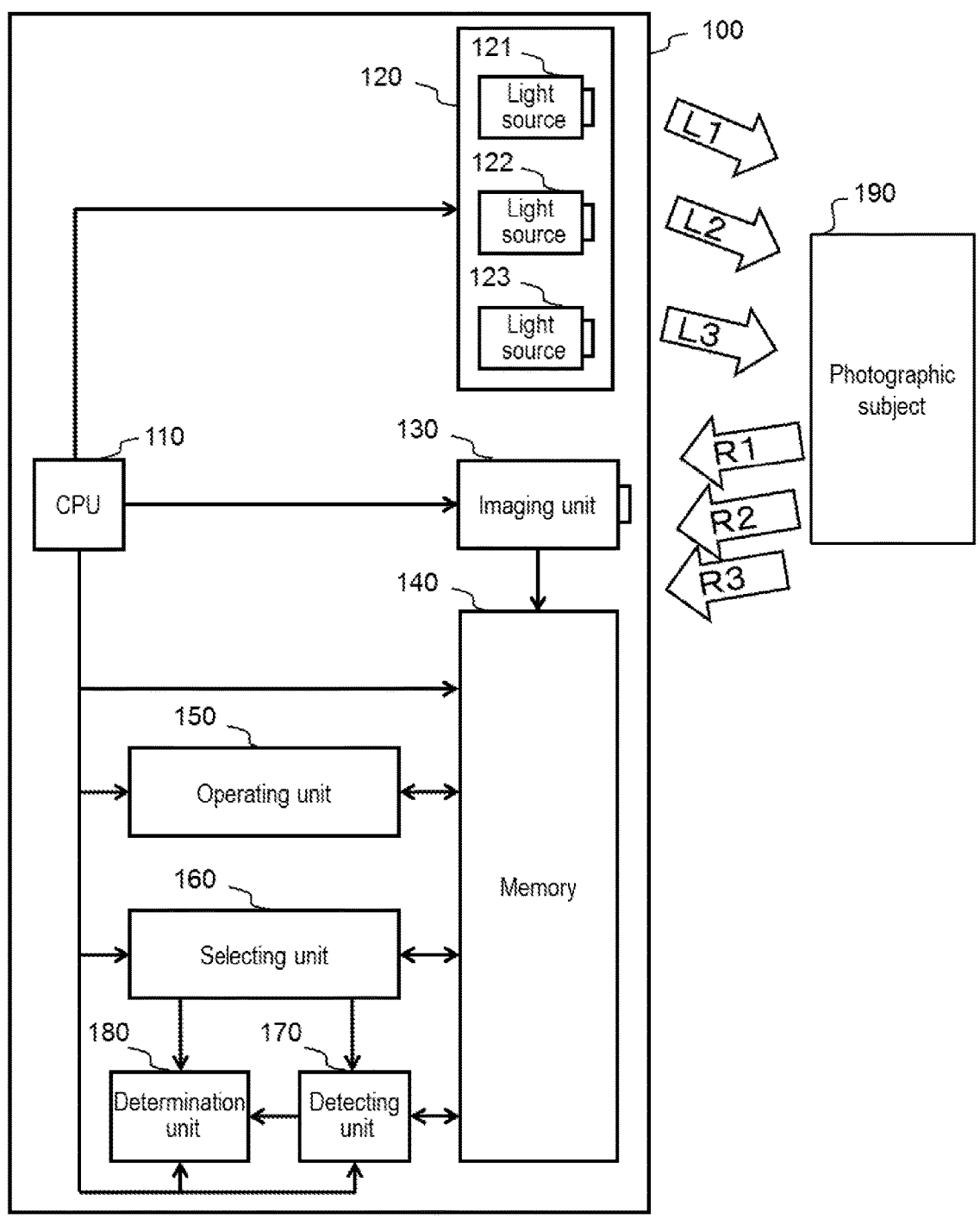
FIG. 2 is a block diagram illustrating a configuration example of an appearance inspection apparatus according to the first exemplary embodiment of the present disclosure.

First Exemplary Embodiment 1-1. Configuration of Appearance Inspection Apparatus FIG. 2 is a block diagram illustrating the configuration of appearance inspection apparatus 100 according to the first exemplary embodiment.

Appearance inspection apparatus 100 includes CPU 110, lighting unit 120, imaging unit 130, memory 140, operating unit 150, selecting unit 160, detecting unit 170, and determination unit 180. Lighting unit 120 has light sources 121, 122, and 123.

CPU 110 controls the operation of each component. For example, CPU 110 controls lighting unit 120 to turn on and off light sources 121, 122, and 123. CPU 110 directs imaging unit 130 to operate imaging. Further, CPU 110 controls the operation of operating unit 150, selecting unit 160, detecting unit 170, and determination unit 180.

Lighting unit 120 has three light sources 121, 122, and 123 that emit single-wavelength light having relative spectral distributions different from one another. Lighting unit 120 irradiates photographic subject 190 with illumination light emitted by the three light sources substantially simultaneously. In this disclosure, the number of light sources is assumed to mean the number of types of light sources that have relative spectral distributions different from one another. Light sources 121, 122, and 123 are single-wavelength light sources with their center wavelengths different from one another. In this embodiment, light source 121 is an LED that emits illumination light L1 having a relative spectral distribution centering on a wavelength of 450 nm. Light source 122 is an LED that emits illumination light L2 having a relative spectral distribution centering on a wavelength of 550 nm. Light source 123 is an LED that emits illumination light L3 having a relative spectral distribution centering on a wavelength of 650 nm. Lighting unit 120 causes light sources 121, 122, and 123 to emit light substantially simultaneously to irradiate photographic subject 190 with three different irradiation lights simultaneously under the control of CPU 110.

Photographic subject 190 reflects illumination light emitted by each light source. Illumination light L1 reflected on photographic subject 190 is assumed to be reflected light R1; illumination light L2, reflected light R2; illumination light L3, reflected light R3. The intensity of reflected light R1 is the product of the intensity of illumination light L1 and the reflectivity of photographic subject 190 at the wavelength of illumination light L1. In the same way, the intensity of reflected light R2 is the product of the intensity of illumination light L2 and the reflectivity of photographic subject 190 at the wavelength of illumination light L2; reflected light R3, illumination light L3. Illumination light L1, L2, and L3 is irradiated onto photographic subject 190 substantially simultaneously. Accordingly, light discharged by photographic subject 190 is a mixture of reflected light R1, R2, and R3.

Imaging unit 130 captures light (i.e., reflected light) discharged by photographic subject 190 in response to multiple illumination light irradiated from multiple light sources of lighting unit 120. Imaging unit 130 has a lens and an imaging element (both unillustrated). The lens forms an image of photographic subject 190 caused by reflected light R1, R2, and R3 onto the imaging element. The imaging element has pixels in the RGB Bayer arrangement, capable of three-color imaging. That is, imaging unit 130 operates as an RGB camera. Imaging unit 130 captures an image of photographic subject 190 as a color image and causes memory 140 to store the image. In this embodiment, imaging unit 130 is an RGB camera including an imaging element with the sensitivity characteristics shown in FIG. 3.

Figure 3:
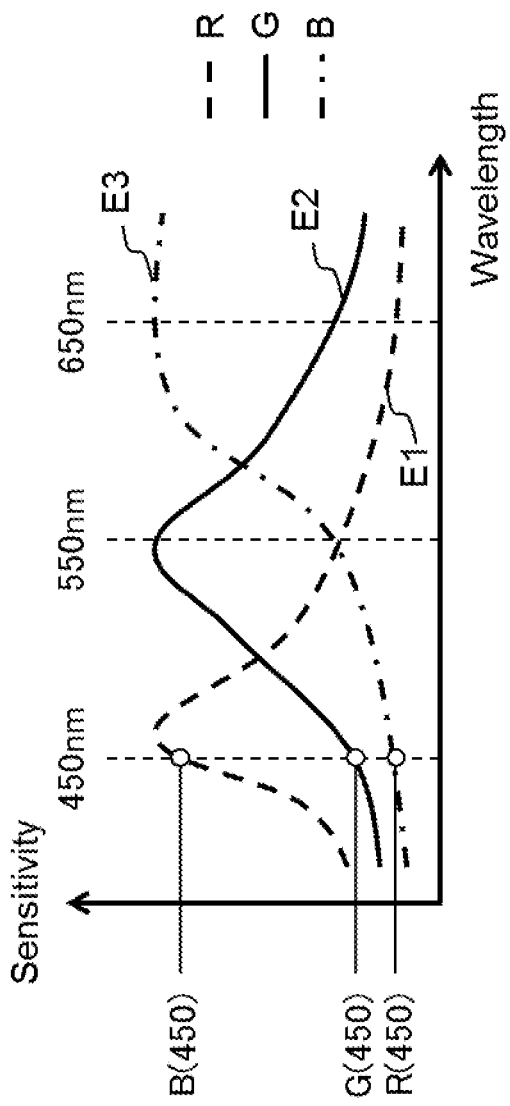
FIG. 3 illustrates the spectral sensitivity characteristic of the imaging unit of the appearance inspection apparatus shown in FIG. 2.

FIG. 3 illustrates the sensitivity characteristics of imaging unit 130. In other words, FIG. 3 is also an example of the spectral sensitivity characteristics of a color filter for each pixel of the imaging element. The vertical axis represents sensitivity; the horizontal axis, wavelength (nm). Broken line E1 represents the sensitivity characteristics of band R of the RGB camera; solid line E2, the sensitivity characteristics of band G; dot-and-dash line E3, the sensitivity characteristics of band B. Imaging unit 130 features that the spectral sensitivity characteristics of three colors largely overlap with one another as shown in FIG. 3 and non-zero values are observed in multiple colors whichever wavelength of single-wavelength light is observed. Imaging unit 130 simultaneously captures reflected light R1, R2, and R3 corresponding to multiple illumination light L1, L2, and L3 simultaneously irradiated onto photographic subject 190. Imaging unit 130 has sensitivity to all reflected light R1, R2, and R3, and thus pixels of each color observe light in a state of reflected light R1, R2, and R3 mixed together.

Next, a description is made of information about the sensitivity characteristics of imaging unit 130 for the RGB colors at a certain wavelength. It is assumed that a certain wavelength is λ(nm); the spectral sensitivity characteristics of imaging unit 130 in band R are R(λ); the spectral sensitivity characteristics in band G are G(λ); the spectral sensitivity characteristics in band B are B(λ). Then, the sensitivity characteristics of imaging unit 130 for each color at the wavelength can be expressed by RGB vector (B(λ), G(λ), R(λ)). As an example, FIG. 3 shows RGB vector (B(450), G(450), R(450)) at wavelength λ of 450 nm.

Imaging unit 130 has spectral sensitivity characteristics of three colors largely overlapping with one another as shown in FIG. 3. Accordingly, whichever combination of three wavelengths is chosen within the range of wavelengths shown in FIG. 3, information about the sensitivity characteristics of imaging unit 130 for each color at the wavelengths is linearly independent of one another. That is, information about the sensitivity characteristics of imaging unit 130 of light sources 121, 122, and 123 for each color at the wavelengths is linearly independent of one another. Concretely, the center wavelengths of light sources 121, 122, and 123 are respectively 450 nm, 550 nm, and 650 nm, and thus RGB vectors (B(450), G(450), R(450)), (B(550), G(550), R(550)), and (B(650), G(650), R(650)), which are information about the sensitivity characteristics of imaging unit 130 of light sources 121, 122, and 123 for each color at the wavelengths, are linearly independent of one another.

Memory 140 stores an image captured by imaging unit 130 and process results of operating unit 150 and detecting unit 170. Memory 140 is used as working memory for operating unit 150, selecting unit 160, detecting unit 170, and determination unit 180. Further, memory 140 stores information about the sensitivity characteristics of imaging units 130 of light sources 121, 122, and 123 for the RGB colors. This information is related to the direction of the RGB vectors where light sources 121, 122, and 123 are imaged by imaging unit 130. In other words, this information is composed of information about the relative spectral distributions of light sources 121, 122, and 123 and a value containing the spectral sensitivity characteristics of imaging unit 130. Each RGB vector is normalized so that its length is one. Here, information about the sensitivity characteristics of imaging units 130 of the light sources for the RGB colors has been acquired in advance. For example, the information has been acquired in advance by normalizing RGB values obtained by directly imaging the light sources by imaging unit 130.

Operating unit 150 uses information about the sensitivity characteristics of imaging unit 130 of the light sources for the RGB colors, stored in memory 140, to perform a computing process on an image captured by imaging unit 130. Through this process, operating unit 150 separates the image into multiple images each containing only reflected light corresponding to each light source. For example, reflected light corresponding to light source 121 is reflected light R1; light source 122, reflected light R2; light source 123, reflected light R3. That is, reflected light corresponding to each light source means reflected light caused by irradiated light from each light source.

As described above, operating unit 150 uses information about the sensitivity characteristics of imaging unit 130 of light sources 121, 122, and 123 for the RGB colors to perform a computing process (described later) on the image captured by imaging unit 130. As a result, operating unit 150 calculates the captured image to derive a single-wavelength image containing only reflected light R1, that containing only reflected light R2, and that containing only reflected light R3, for the respective wavelengths of the light sources, and separates these single-wavelength images from one another, and then causes memory 140 to store them.

Selecting unit 160 selects one or more single-wavelength images from the three separated by operating unit 150 under the control of CPU 110. Then, selecting unit 160 reads a single-wavelength image chosen in memory 140, and provides it to detecting unit 170 and determination unit 180. In this embodiment, a single-wavelength image selected by selecting unit 160 is determined in advance.

Detecting unit 170 uses the single-wavelength image provided from selecting unit 160 under the control of CPU 110 to detect information about a specific area of photographic subject 190. For example, if photographic subject 190 is a tomato and a bruise of the fruit is to be observed, information about the fruit is to be detected with the fruit being a specific area. Further, detecting unit 170 provides the information about a specific area to determination unit 180 as a detection result and causes memory 140 to store the information.

Determination unit 180 uses the detection result provided from detecting unit 170 to determine whether a characteristic part is present in the specific area of photographic subject 190. Where photographic subject 190 is a tomato, determination unit 180 determines whether a bruise is present on the surface (i.e., the specific area) of the fruit.

Note that, in this disclosure, light sources used for imaging photographic subject 190 are light sources 121, 122, and 123 only, and imaging is performed in a darkroom.

1-2. Operation 1-2-1. Operation of Appearance Inspection Apparatus

A description is made of the operation of appearance inspection apparatus 100 configured as above.

Figure 4:
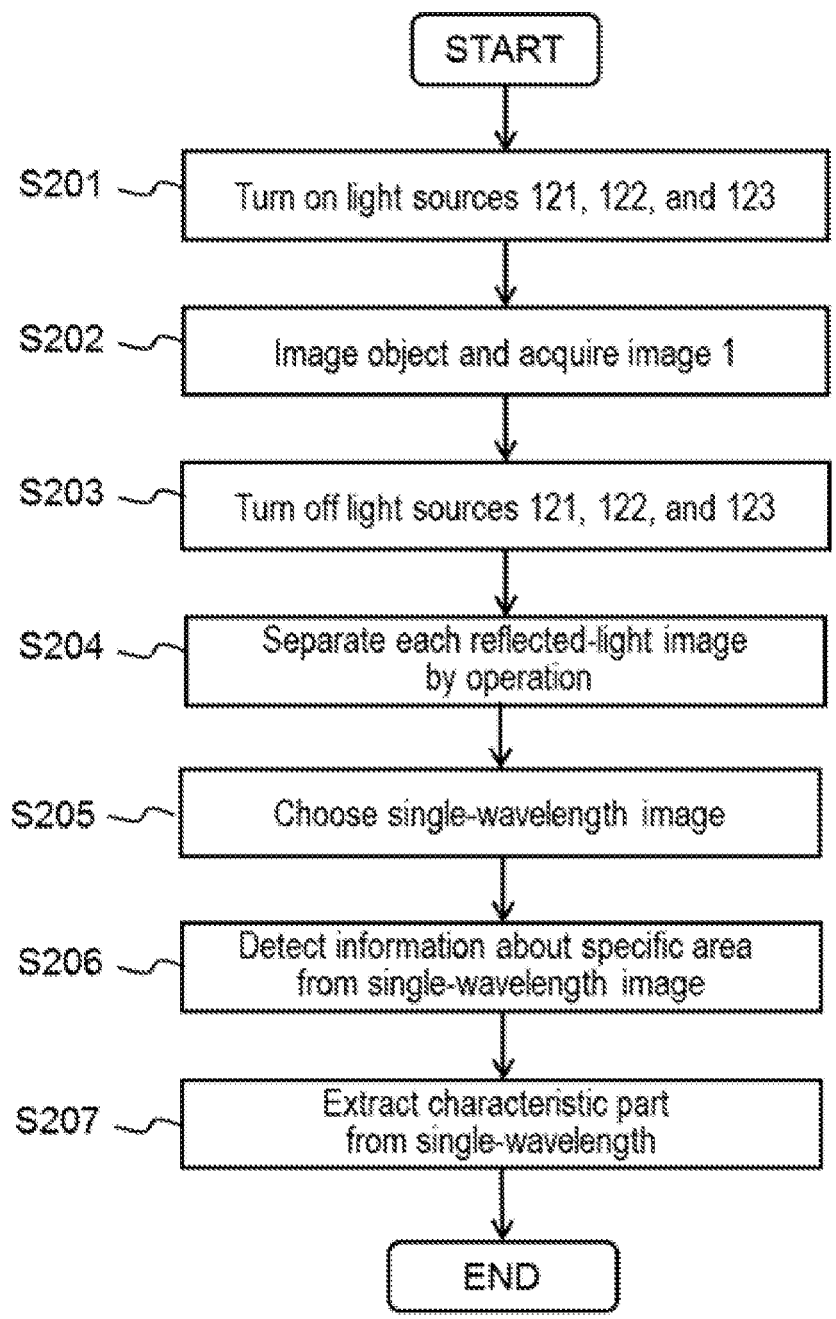
FIG. 4 is a flowchart for illustrating the operation of the appearance inspection apparatus shown in FIG. 2.

FIG. 4 is a flowchart for describing the operation of appearance inspection apparatus 100.

In step S201, CPU 110 controls lighting unit 120 to turn on light sources 121, 122, and 123. Lighting unit 120 turns on light sources 121, 122, and 123 under this control to irradiate photographic subject 190 with illumination light L1, L2, and L3 substantially simultaneously.

In step S202, CPU 110 causes imaging unit 130 to image photographic subject 190 with illumination light L1, L2, and L3 irradiated simultaneously. Imaging unit 130 captures observation light produced by mixing reflected light R1, R2, and R3 reflected by photographic subject 190 to acquire captured image P. Captured image P contains reflected light R1, R2, and R3. Imaging unit 130 causes memory 140 to store captured image P.

In step S203, CPU 110 controls lighting unit 120 to turn off light sources 121, 122, and 123 when imaging in step 202 ends. Lighting unit 120 turns off light sources 121, 122, and 123 under this control.

In step S204, CPU 110 controls operating unit 150. Operating unit 150 uses information about the sensitivity characteristics of imaging unit 130 of each light source for the RGB colors under this control to separate captured image P stored in memory 140 into multiple images containing only reflected light corresponding to each light source. Specifically, operating unit 150 separates captured image P into three images including a single-wavelength image containing only reflected light R1, that containing only reflected light R2, and that containing only reflected light R3, to cause memory 140 to store the image.

In step S205, CPU 110 controls selecting unit 160. Under this control, selecting unit 160 selects and reads one or more single-wavelength images from three of those stored in memory 140, and provides them to detecting unit 170 and determination unit 180.

In step S206, CPU 110 controls detecting unit 170. Under this control, detecting unit 170 detects information about a specific area of photographic subject 190 from the one or more single-wavelength images provided from selecting unit 160. Further, detecting unit 170 outputs the information about a specific area detected to determination unit 180.

In step S207, CPU 110 controls determination unit 180. Under this control, determination unit 180 determines whether a predetermind characteristic part is present in photographic subject 190 from the one or more single-wavelength images provided from selecting unit 160. In other words, determination unit 180 uses information about a specific area output from detecting unit 170 and the one or more single-wavelength images provided from selecting unit 160, to extract a predetermind characteristic part, if any, in the single-wavelength images. Determination unit 180 observes a state of photographic subject 190 referring to the extraction result.

To continuously image a subject, step S203 may be skipped. Instead, imaging and operation for a next photographic subject may be performed while light sources 121, 122, and 123 remain on followed by executing step S203 at any timing.

1-2-2. Calculating a Reflected Light Image of Each Wavelength

A detailed description is made of the operation in step S204. This operation is performed for each pixel of captured image P. For imaging elements of the Bayer arrangement structure with multiple color filters arranged in a checkered pattern, as in this embodiment, one pixel includes only one-color value. For this reason, by means of interpolation using information about surrounding pixels, values of pixels between the RGB colors are created, and a process for making one pixel have multiple colors is performed in advance. To make one pixel have multiple colors, any method, besides the above, may be used. For example, an imaging element that includes multiple colors in one pixel from a state of a device, or a dichroic mirror may be used to distribute light of each color to monochrome imaging elements coaxially disposed.

A description is made assuming that pixel p is one certain pixel as an operation target among pixels in captured image P. An RGB vector (i.e., an RGB value) is recorded on each pixel.

The RGB vector of pixel p is the sum of RGB vectors of reflected light R1, R2, and R3. Here, light sources 121, 122, and 123 are narrow-band LEDs. Accordingly, the directions of the RGB vectors of reflected light R1, R2, and R3 are regarded as the same as the directions of an RGB vector that is information about the sensitivity characteristics of imaging units 130 of light sources 121, 122, and 123 for each color, respectively. In other words, the direction of the RGB vector of reflected light R1 can be regarded as the same as the direction of an RGB vector that is information (held in memory 140) about the sensitivity characteristics of imaging unit 130 of light source 121 for the RGB colors. Similarly, the direction of the RGB vector of reflected light R2 can be regarded as the same as the direction of an RGB vector that is information (held in memory 140) about the sensitivity characteristics of imaging unit 130 of light source 122 for the RGB colors; and the direction of the RGB vector of reflected light R3 can be regarded as the same as the direction of an RGB vector that is information (held in memory 140) about the sensitivity characteristics of imaging unit 130 of light source 123 for the RGB colors.

Here, it is assumed that information about the sensitivity characteristics of imaging unit 130 of light source 121 for each color is RGB vector r1; information about the sensitivity characteristics of imaging unit 130 of light source 122 for each color is RGB vector r2; and information about the sensitivity characteristics of imaging unit 130 of light source 123 for each color is RGB vector r3. By using what is described above, RGB vector Ip of pixel p is expressed as a linear combination of RGB vectors r1, r2, and r3. That is, if RGB vector Ip of pixel p is (IpR, IpG, IpB), RGB vector r1 stored in memory 140 is (r1R, r1G, r1B), and RGB vector r3 is (r3R, r3G, r3B), then vector Ip is expressed by the next expression.

Expression (1)

$$\begin{pmatrix} Ip_R \\ Ip_G \\ Ip_B \end{pmatrix} = w_1 \begin{pmatrix} r1_R \\ r1_G \\ r1_B \end{pmatrix} + w_2 \begin{pmatrix} r2_R \\ r2_G \\ r2_B \end{pmatrix} + w_3 \begin{pmatrix} r3_R \\ r3_G \\ r3_B \end{pmatrix} \quad (1)$$

Here, w1 is the weight of vector r1; w2, the weight of vector r2; w3, the weight of vector r3.

Expression (1) is a simultaneous equation of three expressions in three unknowns (w1, w2, and w3). Information about the sensitivity characteristics of imaging unit 130 of each light source for the RGB colors is linearly independent. Accordingly, the simultaneous equation can be solved, and the unknowns can be calculated. Unknowns w1, w2, and w3 can be calculated by solving the equation using any method. For example, the equation is expressed by a matrix, and operation using an inverse matrix can be used to solve the equation.

For another example, the RGB vector of reflected light R1 on pixel p can be calculated from the product of w1 and vector r1. Similarly, the RGB vector of reflected light R2 on pixel p can be calculated from the product of w2 and vector r2; the RGB vector of reflected light R3 on pixel p can be calculated from the product of w3 and vector r3. These values correspond to the first, second, and third terms, respectively, of the right side of expression (1).

By executing the above operation on all the pixels, the two-dimensional distribution information about the RGB vectors of respective reflected light R1, R2, and R3 can be calculated from captured image P. In other words, captured image P provides a single-wavelength image containing only reflected light R1; that containing only reflected light R2; and that containing only reflected light R3. Captured image P thus can be separated into a single-wavelength image containing only reflected light R1; that containing only reflected light R2; and that containing only reflected light R3. Each single-wavelength image separated has an RGB vector for each pixel, and thus is a color image.

To change the wavelength of a light source to be used, any one or more of light sources 121, 122, and 123 may be changed to another single-wavelength light source with a wavelength different from any of light sources 121, 122, and 123. If a light source has been changed, information about the sensitivity characteristics of imaging unit 130 of the light source changed for the RGB colors is stored in memory 140 at this time or in advance.

As described above, imaging unit 130 has spectral sensitivity characteristics of the three RGB colors largely overlapping with one another. Accordingly, whichever combination of three wavelengths is chosen in the range of wavelengths shown in FIG. 3, information about the sensitivity characteristics of imaging unit 130 for each color at the wavelengths is linearly independent of one another. Accordingly, after a freely chosen light source has been changed, information about the sensitivity characteristics of imaging unit 130 of each light source for each color is linearly independent of one another. This allows operating unit 150 to solve the equation. In other words, imaging unit 130 has spectral sensitivity characteristics of the three colors largely overlapping with one another as shown in FIG. 3. Accordingly, whichever combination of three wavelengths is chosen, information about the sensitivity characteristics of imaging unit 130 for each color at the wavelengths is linearly independent of one another. This allows any combination of wavelengths to be chosen freely only by changing the wavelength of lighting without changing imaging unit 130 itself. This thus provides a high flexibility in the selection of wavelengths to be used. Consequently, an optimum wavelength for observation can be freely chosen and changed in response to circumstances.

1-2-3. Selection of Single-Wavelength Image

Next, a description is made of the operation of selecting unit 160. Selecting unit 160 reads one or more single-wavelength images determined beforehand from memory 140 and provides them to detecting unit 170 and determination unit 180 under the control of CPU 110.

As shown in FIG. 1, a tomato has spectral distributions different depending on an area of the tomato. For example, the intensity of reflected light at the stem is different from that at the fruit near a wavelength of 550 nm, and this magnitude relationship is reversed near a wavelength of 650 nm. Accordingly, calculating the two ratios allows the stem and the fruit of the tomato to be discriminated. To detect a bruise on the surface of the fruit, the ratios of the intensity of reflected light at the bruise to that of the fruit near wavelengths of 550 nm and 650 nm are calculated to increase the contrast at the bruise.

The center wavelengths of light sources 121, 122, and 123 are respectively 450 nm, 550 nm, and 650 nm. Thus in this embodiment, setting is made to choose single-wavelength images of reflected light R2 and R3 for detecting unit 170; those of reflected light R1 and R3, for determination unit 180.

1-2-4. Detection of Specific Area

Next, a description is made of the operation of detecting unit 170. Detecting unit 170 is provided with single-wavelength images of reflected light R2 and R3 from selecting unit 160. Detecting unit 170 uses pixel values corresponding to the same positions in single-wavelength images of reflected light R2 and R3 to calculate a ratio for each pixel, and generates an image with the ratio calculated being a pixel value at its original position. Detecting unit 170 binarizes the value of each pixel of the image generated to generate a binary image. The detecting unit outputs this binary image as a detection result.

Figure 5:
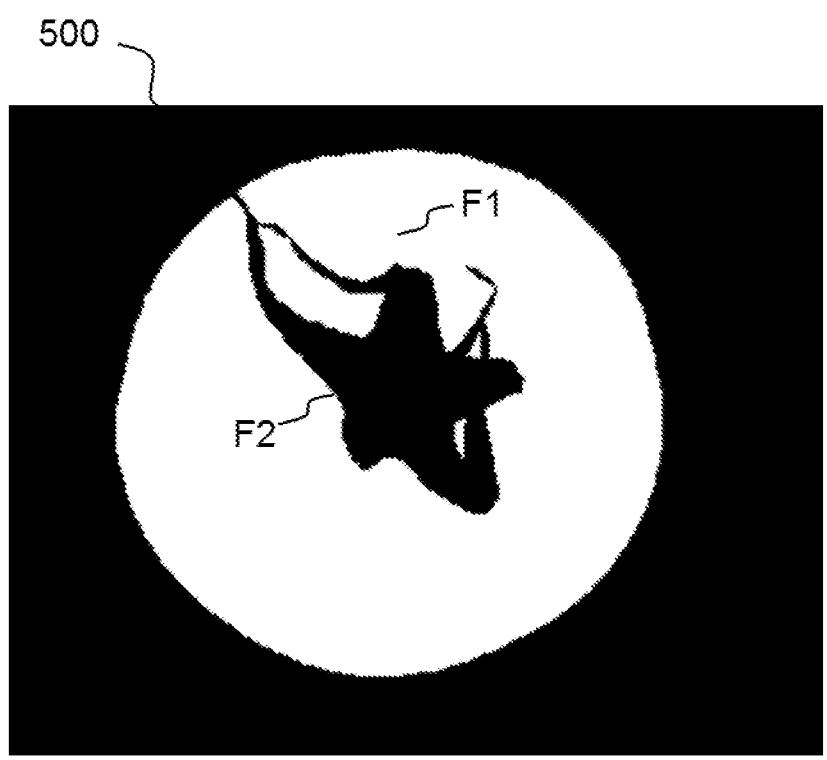
FIG. 5 illustrates an example of a binary image generated by the detecting unit of the appearance inspection apparatus shown in FIG. 2.

FIG. 5 is an example of binary image 500 generated by detecting unit 170. In binary image 500, white region F1 represents the fruit region of a tomato, and black region F2 inside white region F1 represents the stem region. As shown in FIG. 5, a binary image proves to be generated where fruit region F1 (i.e., a specific area of the tomato) and stem region F2 (i.e., an unspecific area) are separated from each other.

1-2-5. Extracting a Characteristic Part of an Image

Next, a description is made of the operation of determination unit 180. In this embodiment, the description is made of a characteristic part as a bruise present in the fruit region that is a specific area detected by detecting unit 170.

First, determination unit 180 uses pixel values corresponding to the same positions in the single-wavelength images of reflected light R1 and R3 provided from selecting unit 160 to calculate ratios for each pixel, and generates an image with the ratios calculated being pixel values at their original positions. Next, determination unit 180 detects an edge in the image generated, and produces a candidate image of a bruise with the edge enhanced. If photographic subject 190 has a bruise, the candidate image of a bruise contains the contour of photographic subject 190 and the edge of the bruise. In this case, the edge of the bruise is an example of the amount of image characteristics of a characteristic part. Determination unit 180 uses the bruise-candidate image and information about the specific area detected by detecting unit 170 to exclude an edge corresponding to the contour of photographic subject 190 from the bruise-candidate image to extract a characteristic part (i.e., a bruise).

Where photographic subject 190 is a tomato for example, edges in a bruise-candidate image are of a bruise as well as of contours of the stem and fruit of the tomato. Determination unit 180 uses the fruit region in the binary image as a mask image to calculate the logical AND of the candidate image and the mask image. This allows determination unit 180 to exclude edges detected from the contours of the stem and the fruit of the tomato to extract only bruises in the fruit part.

In the description above, detecting unit 170 and determination unit 180 use pixel values corresponding to the same positions of the two single-wavelength images provided from selecting unit 160 to calculate a ratio for each pixel. As described in reference to FIG. 1, however, a tomato has spectral distributions different depending on an area (fruit, stem, or bruise). Using the difference between parts allows detecting a specific area. Accordingly, detecting unit 170 and determination unit 180 can detect a specific area and a characteristic part in the specific area even from one single-wavelength image. For example, the fruit region of the tomato can be separated from the stem region from a single-wavelength image near a wavelength of 650 nm. Here, more single-wavelength images to be used, namely more single-wavelength images for each component of a single wavelength, provide higher detection accuracy.

1-3. Summary

Appearance inspection apparatus 100 according to this embodiment includes lighting unit 120, imaging unit 130, memory 140, operating unit 150, and detecting unit 170. Lighting unit 120 has light sources 121, 122, and 123 that emit single-wavelength light with relative spectral distributions different from one another and irradiate photographic subject 190 with illumination light substantially simultaneously. Imaging unit 130 captures light discharged from photographic subject 190 in response to the illumination light irradiated by light sources 121, 122, and 123 substantially simultaneously. Memory 140 stores information about the sensitivity characteristics of imaging unit 130 for the RGB colors. Operating unit 150 uses information about the sensitivity characteristics of imaging unit 130 for each color to separate the image captured by imaging unit 130 into multiple single-wavelength images for each component of a single wavelength. Detecting unit 170 uses one or more single-wavelength images chosen from the multiple single-wavelength images to detect information about a specific area of photographic subject 190.

Appearance inspection apparatus 100 further includes determination unit 180. Determination unit 180 extracts characteristic parts present in photographic subject 190 using one or more single-wavelength images of the multiple single-wavelength images chosen by operating unit 150 and the detection result of detecting unit 170. On this occasion, determination unit 180 selects one or more of the multiple single-wavelength images and extracts the amount of image characteristics corresponding to characteristic parts present in a specific area detected by detecting unit 170 using edge detection.

This allows operating unit 150 to acquire multiple single-wavelength images from an image captured one time. Detecting unit 170 can detect information about a specific area using a single-wavelength image optimum for detecting each area. Determination unit 180 can exclude parts other than characteristic parts well accurately from multiple characteristic parts by using a result of detecting unit 170.

Accordingly, the simple configuration helps reduce imaging time and extract characteristic parts efficiently, eventually allowing speedy, accurate appearance inspection of photographic subject 190.

Second Exemplary Embodiment 2-1. Configuration of Appearance Inspection Apparatus The configuration of an appearance inspection apparatus according to the second exemplary embodiment is the same as that according to the first embodiment shown in FIG. 2. This embodiment is different from the first only in the operation of detecting unit 170. In this embodiment, a description is made mainly about the operation of detecting unit 170.

Detecting unit 170 detects a specific area and changes the detection result to a binary image for outputting under the control of CPU 110, based on one or more of the single-wavelength images provided from selecting unit 160, using a discrimination boundary determined by machine learning.

2-2. Operation

Subsequently, a description is made of the operation of appearance inspection apparatus 100 according to this embodiment.

2-2-1. Detecting a Specific Area

Figure 6:
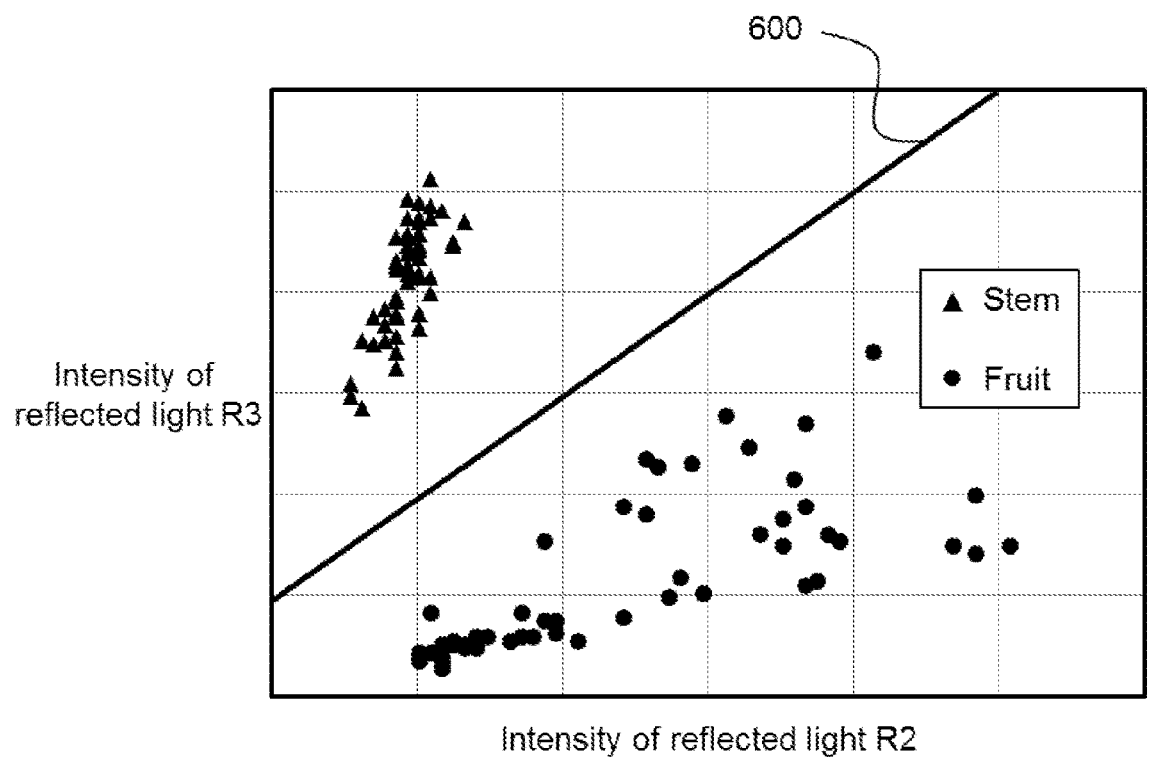
FIG. 6 illustrates an example of a discrimination boundary in the detecting unit of an appearance inspection apparatus according to the second exemplary embodiment of the disclosure.

A description is made of the operation of detecting unit 170 referring to FIG. 6. FIG. 6 illustrates an example of a discrimination boundary determined by detecting unit 170 of this embodiment. The vertical axis represents the intensity of reflected light R3; the horizontal axis, the intensity of reflected light R2. Black dots and black triangles indicate classification on a plane, of pairs of the intensities of reflected light R2 and R3 at the same positions of pixels corresponding to the fruit and stem in single-wavelength images due to reflected light R2 and R3. A black dot indicates a pixel at a position corresponding to the stem; a black triangle, the fruit.

As shown in FIG. 6, the distributions of pixels of the fruit and the stem of a tomato helps determine a discrimination boundary that separates the fruit from the stem as shown by line 600. To determine the discrimination boundary, machine learning (e.g., a support vector machine) can be used. This discrimination boundary allows separating the fruit from the stem of a tomato. More specifically, detecting unit 170 can generate a binary image in which the fruit is separated from the stem in binary based on a discrimination boundary from the relationship between pixel values at each pixel corresponding to the same positions in the single-wavelength image of reflected light R2 and R3. In this embodiment as well, detecting unit 170 uses two single-wavelength images. However, as shown in FIG. 6, even only the intensity of a single-wavelength image of reflected light R3 for example allows roughly separating the fruit from the stem.

2-3. Summary

In appearance inspection apparatus 100 according to this embodiment, detecting unit 170 determines a discrimination boundary that separates multiple specific areas from a single-wavelength image separated by operating unit 150 using machine learning.

Resultingly, detecting unit 170 uses a discrimination boundary corresponding to the characteristics of photographic subject 190 to generate an image showing a specific area detected.

Accordingly, the simple configuration helps reduce imaging time and extract characteristic parts efficiently, eventually allowing speedy, accurate appearance inspection of photographic subject 190.

Figure 7:
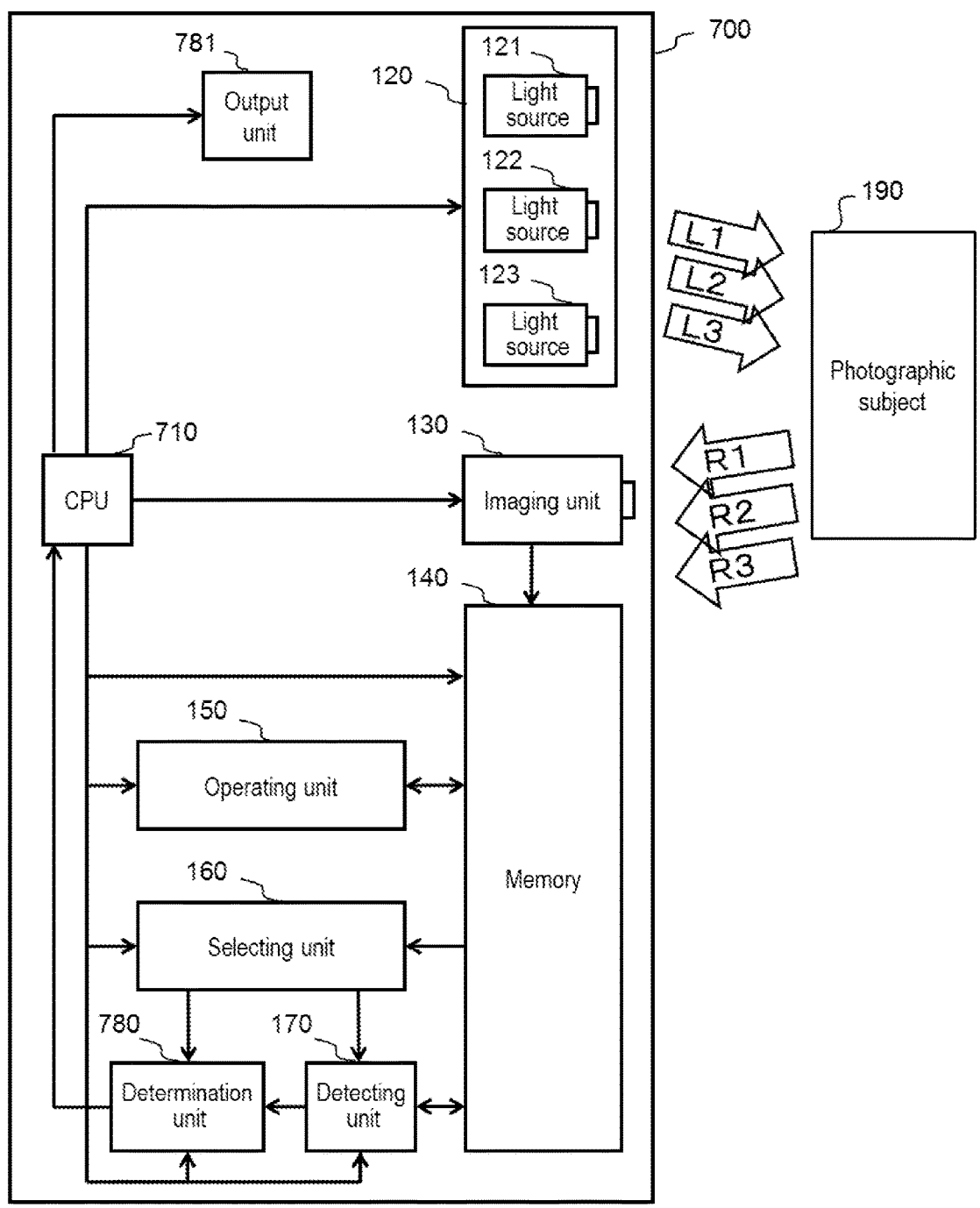
FIG. 7 is a block diagram illustrating a configuration example of an appearance inspection apparatus according to the third exemplary embodiment of the disclosure.

Third Exemplary Embodiment 3-1. Configuration of Appearance Inspection Apparatus FIG. 7 is a block diagram illustrating an example configuration of appearance inspection apparatus 700 according to the third exemplary embodiment. In FIG. 7, a component that operates in the same way as that in FIG. 2 is given the same reference mark and its detailed description is omitted. Appearance inspection apparatus 700 further includes output unit 781 in addition to the components of the first embodiment shown in FIG. 2. Appearance inspection apparatus 700 has CPU 710 and determination unit 780 instead of CPU 110 and determination unit 180. CPU 710 and determination unit 780 operate differently from CPU 110 and determination unit 180. Hereinafter, a description is made mainly about the operation of CPU 710, determination unit 780, and output unit 781.

CPU 710 controls the operation of each component in the same way as the first embodiment. CPU 710 causes output unit 781 to output a result obtained by determination unit 780.

Determination unit 780 extracts characteristic parts in an image from information about a specific area provided from detecting unit 170.

Output unit 781, an information display device such as an LCD monitor, outputs (displays) information output from CPU 710 to the display unit. Otherwise, output unit 781 is an interface or an output terminal that outputs a signal indicating that the image contains a characteristic part.

3-2. Operation

Subsequently, a description is made of the operation of appearance inspection apparatus 700.

3-2-1. Extracting a Characteristic Part in Image

First, a description is made of the operation of determination unit 780. Determination unit 780 detects a characteristic part present in photographic subject 190 in the same way as determination unit 180 described in the first embodiment. Determination unit 780, when detecting a characteristic part, outputs the extraction result to CPU 710. To output a result, the following means can be used for example. That is, determination unit 780 is connected to a port (unillustrated) of CPU 710 and a high or low signal is provided to the port according to the presence or absence of an extraction result.

Where photographic subject 190 is a tomato, determination unit 780, if successfully extracting a bruise in the fruit, outputs the result to CPU 710.

3-2-2. Displaying Information

CPU 710 controls output unit 781 in response to an extraction result output from determination unit 780. Concretely, when determination unit 180 has determined that a bruise is present in the fruit and output unit 781 is an information display device, CPU 710 causes output unit 781 to display information indicating the fact.

Figure 8:
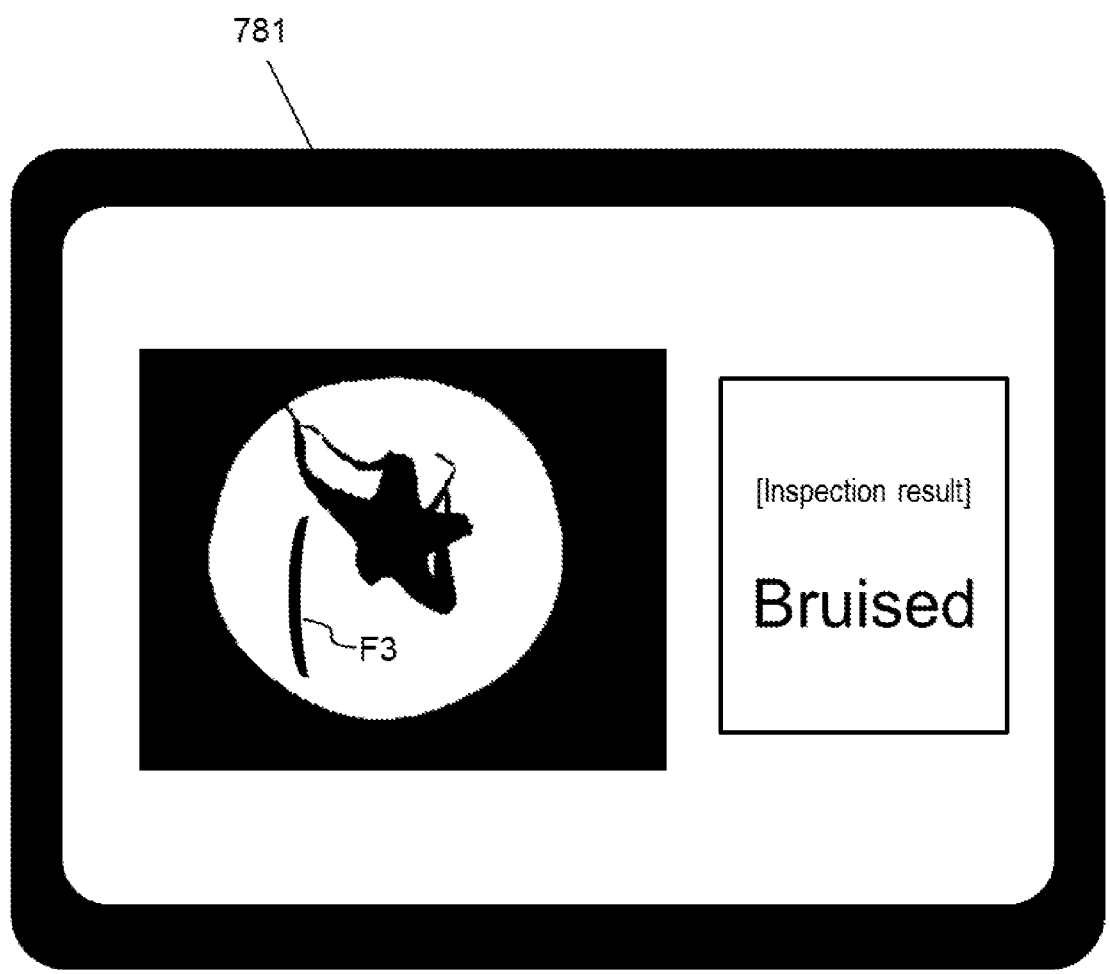
FIG. 8 illustrates an example of display by the output unit of the appearance inspection apparatus shown in FIG. 7.

FIG. 8 illustrates an example of display on output unit 781. Output unit 781 displays the presence or absence of a bruise in character on the screen; alternatively, displays an image of a bruised (region F3 in FIG. 8) fruit. On this occasion, the bruise may be displayed highlighted by changing color or blinking at the part of the bruise.

Output unit 781 may display the quantity and/or the type of bruises. In such a case, determination unit 780, besides extracting a bruise, further determines the quantity and/or the type of bruises and provides the result to CPU 710. Alternatively, the following process may be executed (unillustrated). That is, determination unit 780 causes memory 140 to temporarily store a bruise image extracted by determination unit 780, and when CPU 710 receives information indicating that a bruise is present in the fruit for example, CPU 710 analyzes the bruise image stored in memory 140 to determine the quantity and/or the type of bruises.

3-2-3. Outputting Information

Where output unit 781 is an interface or an output terminal, CPU 710 sends a signal indicating that the image contains a characteristic part, to output unit 781 in response to the extraction result output from determination unit 780. Concretely, when determination unit 780 has determined that a bruise is present in the fruit, CPU 710 outputs a signal indicating the fact to output unit 781. Output unit 781 is electrically connected to another apparatus. An apparatus connected to output unit 781 is a tomato rejecter for example. When imaging unit 130 images a tomato and determination unit 780 detects a bruise in the captured image while the tomato as photographic subject 190 is being conveyed by a conveyor belt for example, the rejecter can reject the bruised tomato according to a signal from output unit 781.

3-3. Summary

In appearance inspection apparatus 700, determination unit 780 outputs an extraction result to CPU 710, and CPU 710 outputs (displays) the extraction result to output unit 781 in response to the result.

This shows an observer a result and its details of extracting a characteristic part, or transmits the information to another device.

Although unillustrated, CPU 710 may output information about a result of detecting by detecting unit 170 to output unit 781. Where photographic subject 190 is a tomato for example, the following process may be performed. That is, CPU 710 calculates the area ratio of the stem region to the fruit region. If the ratio exceeds a predetermind threshold, CPU 710 causes output unit 781 to output information indicating an abnormal state. Besides, if a substance other than a tomato is detected, CPU 710 causes output unit 781 to output information indicating the presence of a foreign substance. Alternatively, CPU 710 may output information about results detected by both determination unit 780 and detecting unit 170.

Figure 9:
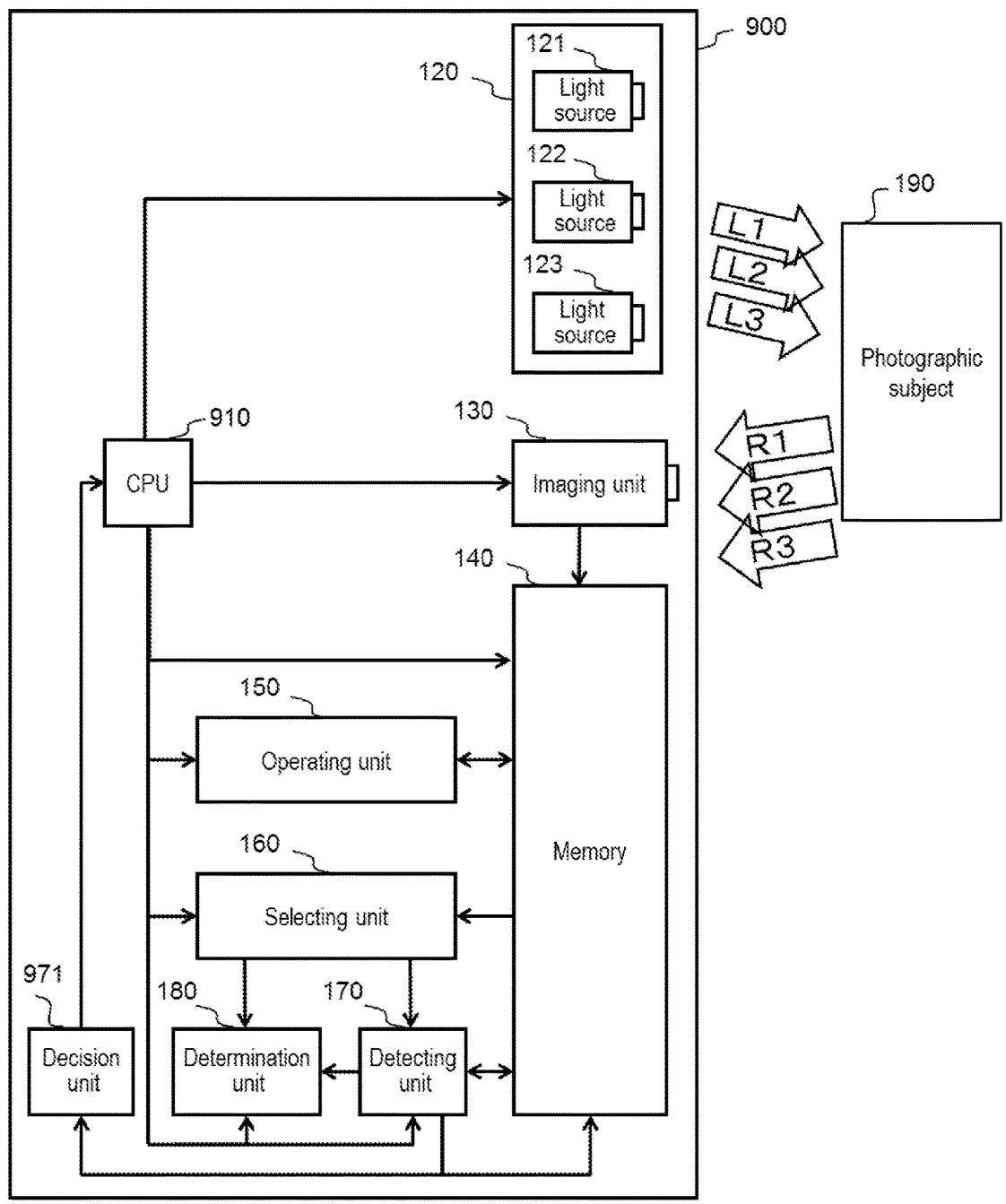
FIG. 9 is a block diagram illustrating a configuration example of an appearance inspection apparatus according to the fourth exemplary embodiment of the disclosure.

Fourth Exemplary Embodiment 4-1. Configuration of Appearance Inspection Apparatus FIG. 9 is a block diagram illustrating an example configuration of appearance inspection apparatus 900 according to the fourth exemplary embodiment.

The configuration of appearance inspection apparatus 900 is different from that according to the first embodiment shown in FIG. 2 in that lighting unit 120 and detecting unit 170 operate differently; in that appearance inspection apparatus 900 has CPU 910 instead of CPU 110, and further has decision unit 971. CPU 910 operates differently from CPU 110. The other configurations are the same as those of appearance inspection apparatus 100 shown in FIG. 2. Accordingly, only parts different from those of the first embodiment are described below.

CPU 910 independently controls the light-source intensities of light sources 121 through 123 based on information about their intensities received from decision unit 971.

Lighting unit 120 irradiates photographic subject 190 with illumination light from light sources 121 through 123 with specified light-source intensities under the control of CPU 910.

Detecting unit 170 provides the detection result to decision unit 971 under the control of CPU 910.

Decision unit 971 reads each single-wavelength image extracted by operating unit 150, from memory 140. Decision unit 971 then decides the intensity of each light source for next imaging, from each intensity of reflected light in the mask image region of a specific area provided from detecting unit 170. Further, decision unit 971 outputs information about light-source intensity decided to CPU 910.

4-2. Operation

Subsequently, a description is made of the operation of appearance inspection apparatus 900.

4-2-1. Deciding Light-Source Intensity

First, the CPU executes the same operation as in the first embodiment shown in FIG. 4 with freely determined light-source intensity, and operating unit 150 calculates a single-wavelength image corresponding to the wavelength of each light source. Next, operating unit 150 outputs each single-wavelength image calculated, to decision unit 971 through memory 140 or directly. Decision unit 971 calculates the average value of the intensities inside a specific area at the spatially same position for each single-wavelength image having been input. In other words, decision unit 971 calculates the average value of the intensities in specific region A inside the single-wavelength image corresponding to the wavelength of light source 121. Further, decision unit 971 calculates the average value of the intensities in specific region A inside the single-wavelength image corresponding to the wavelength of light source 122, and to light source 123. For example, the fruit region in a binarized image provided from detecting unit 170 is specified as specific region A.

Decision unit 971 decides light-source intensity of each light source for next imaging using the intensity of specific region A inside each single-wavelength image calculated. For example, the intensity of each light source is assumed to be the same for the first imaging. Assumption is made of a case where a photographic subject has been imaged that has reflectivity to the wavelength of light source 121 relatively lower than that to the wavelength of light sources 122 and 123 for example. In this case, the average intensity of the specific region inside the single-wavelength image corresponding to the wavelength of light source 121 is lower than those of light sources 122 and 123. For example, the ratio of the average intensity of the specific region in the single-wavelength image corresponding to the wavelength of light sources 121, 122, and 123 is assumed to be 1:10:10. In this case, the single-wavelength image corresponding to the wavelength of light source 121 has a low signal strength, resulting in a relatively low S/N. Accordingly, decision unit 971 directs CPU 910 to relatively increase the intensity of light source 121 for next imaging. For example, decision unit 971 passes information about the light-source intensity of each light source to CPU 110 so that the light-source intensities of light sources 121, 122, and 123 are respectively 10, 1, and 1 times those for the first imaging.

CPU 910 receives information about the light-source intensity of each light source from decision unit 971 and causes lighting unit 120 to control the light-source intensity of each light source. More specifically, the light-source intensity mentioned above being assumed to be L, the light-source intensity of each light source is controlled so that the light-source intensity of light source 121 is 10L; light source 122, L; light source 123, L. Here, the following operation may be performed. That is, the set intensity for each light source decided by decision unit 971 is stored in memory 140, and CPU 110 reads the set intensity for each light source from memory 140.

Lighting unit 120 receives directions from CPU 910 and irradiate illumination light with a light-source intensity specified for each light source. More specifically, light source 121 irradiates photographic subject 190 with illumination light with a light-source intensity of 10L; light source 122, L; light source 123, L. This part corresponds to step S201 in FIG. 4.

In step S202 and after, the process same as that in the first embodiment is executed to calculate a single-wavelength image corresponding to the wavelength of each light source.

Through the processes described above, the light-source intensity of light source 121, the reflected light of which has been relatively weak, is increased, so is the signal strength of a single-wavelength image corresponding to the wavelength of light source 121 calculated, providing an image with a higher S/N.

In this embodiment, decision unit 971 uses the fruit region in a binarized image provided from detecting unit 170 as a specific region in a single-wavelength image for calculating an intensity. Besides, any spatial position in the single-wavelength image and a region of any shape may be used.

Decision unit 971 calculates the average intensity of a specific region in a single-wavelength image. Besides, a minimum, maximum, or intermediate value for example may be used instead of the average value.

In this embodiment, the light-source intensity of a light source with reflected light of a low intensity is increased. Besides, control may be performed to decrease the light-source intensity of a light source with reflected light of a high intensity.

In this embodiment, decision unit 971 decides the light-source intensity of each light source so that the intensity of each reflected light corresponding to the wavelength of each light source is at roughly the same level. Besides, the light-source intensity of each light source may be changed with any ratio of intensity.

Figure 10:
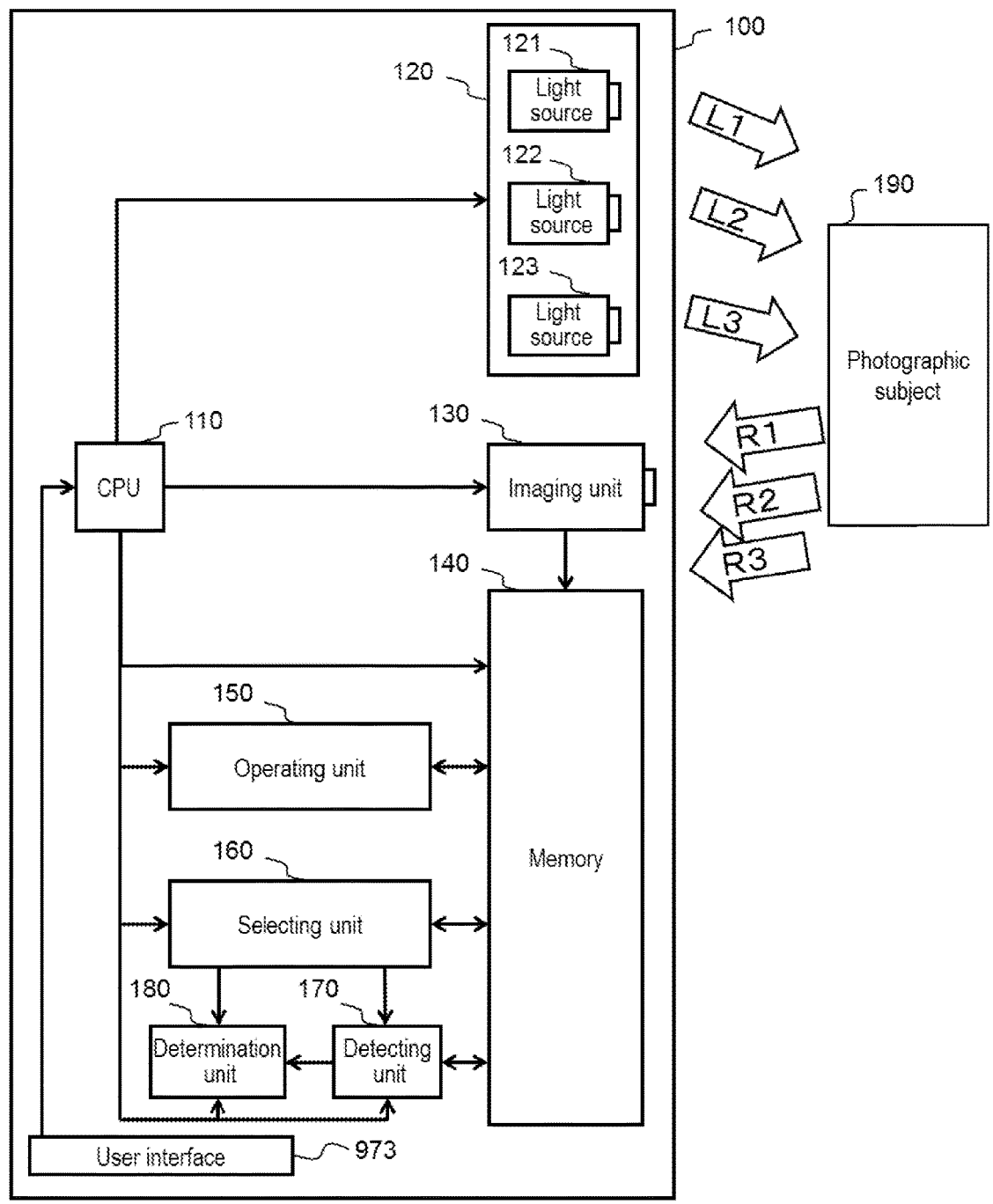
FIG. 10 is a block diagram illustrating another configuration example of the appearance inspection apparatus according to the fourth embodiment of the disclosure.

In this embodiment, decision unit 971 decides the light-source intensity for next imaging according to advance settings after once imaging. Besides, the user may decide the light-source intensity in advance. For example, if the spectral reflectance of a photographic subject is known, the user may set in advance the light-source intensity of a light source corresponding to wavelength with a relatively low reflectivity, to be stronger than the light-source intensity of the other light sources. In this case, as shown in FIG. 10, user interface 973, instead of decision unit 971, is provided that allows inputting in advance the set intensity for each light source. Here, the following operation may be performed. That is, the set intensity for each light source input from user interface 973 is stored in memory 140, and CPU 110 reads the set intensity for each light source from memory 140.

4-3. Summary

In appearance inspection apparatus 900 shown in FIG. 9, decision unit 971 decides the light-source intensity of each light source for next imaging from the reflected-light intensity at a specific region in a single-wavelength image generated by operating unit 150. CPU 910 controls lighting unit 120 using the light-source intensity decided by decision unit 971.

This allows decision unit 971 to detect a light source with low reflectivity and allows CPU 910 to perform control to increase the light-source intensity of the light source with low reflectivity using the detection result of decision unit 971. In other words, the intensity of each light source is independently controllable, and for a light source of the multiple light sources with its reflected light from photographic subject 190 having a relatively low intensity, control is performed to increase the intensity. In this case, CPU 910 functions as a control unit that controls the intensity of at least one of the multiple light sources.

Accordingly, a single-wavelength image separated from a captured image has a stronger signal strength, and thus operating unit 150 can generate an image with a higher S/N ratio, increasing observation accuracy.

Other Exemplary Embodiments

Hereinbefore, the description is made of the first through fourth embodiments for exemplification of the technologies in the disclosure. However, the technologies are not limited to the embodiments, but are also applicable to embodiments that have undergone change, substitution, addition, and/or omission. Besides, some components described in the first through fourth embodiments can be combined to create a new embodiment.

Hereinafter, other embodiments are exemplified. In this disclosure, lighting unit 120 has three light sources that irradiate illumination light simultaneously, and the cameras included in imaging unit 130 can acquire three colors (RGB), but the number of colors is not limited to three. Any number of light sources and colors can be used as long as the number of simultaneous equations exceeds the number of unknowns. After all, the number of light sources that irradiate illumination light simultaneously has only to be equal to or less than the number of colors that the camera can acquire. For example, if the number of colors is four, the number of light sources has only to be equal to or less than four. However, if the number of equations is greater than that of unknowns, namely if the number of light sources that irradiate illumination light simultaneously is smaller than the number of colors that the camera can acquire, a method (e.g., least-square method) for calculating an optimum solution needs to be used. For more light sources and more colors, information about the sensitivity characteristics of an imaging unit of each light source for each color, stored in memory 140 as well needs to be changed appropriately. For example, if the number of colors that the camera can acquire is four, the vector that is information about the sensitivity characteristics of an imaging unit of each light source for each color is a 4-dimantional vector.

An LED is used as a single-wavelength light source; any light source can be used as long as it has a narrow-band relative spectral distribution, such as a light source including laser, monochromator, and an optical filter that passes light of a specific wavelength. In a broad sense, any light source can be used as long as it is regarded that in creating equations the direction of the RGB vector of reflected light (including the spectral reflectance distribution of a photographic subject) is the same as that of the light source.

The center wavelengths of the light sources are 450 nm, 550 nm, and 650 nm; however, light sources of any wavelength may be used.

Imaging is performed in a darkroom; however, environment light may be present. In such a case, a difference image is calculated between a captured image with illumination light irradiated and that not irradiated for example. The difference image contains only reflected light related to illumination light, and thus it can be regarded as substantially equivalent to an image captured in a darkroom.

The length of an RGB vector, which is information about the sensitivity characteristics of imaging unit 130 of each light source for each color, stored in memory 140 is normalized to one; however, the length may be changed to any value. Whatever the length is, the value of weight simply changes accordingly, and thus the product of weight and an RGB vector remains constant in forming a reflected light image.

Besides, the following may be performed. That is, information about the intensity of each light source is acquired, and normalization is performed with a value corresponding to the intensity. For example, the ratio of the intensities of light sources 121 through 123 is assumed to be 1:2:3. Normalization may be performed with the length of an RGB vector (i.e., information about the sensitivity characteristics of imaging unit of each light source 130 for each color) being 1, 2, and 3. Alternatively, normalization may be performed with any length with their ratio being 1:2:3.

As color information, an RGB value is used; besides, any color information may be used. For example, values such as a luminance signal and a color-difference signal that are obtained by linear transformation from an RGB value may be used.

The operation in step S204 is performed for all the pixels; besides, it may be performed for only part of the pixels of an image for example.

The spectroscopic information about light sources 121 and 122 stored in memory 140 is an RGB vector obtained when light sources 121 and 122 are captured by imaging elements, where the RGB vector includes the spectral distributions of light sources 121 and 122 and the spectral sensitivity characteristics of the imaging elements; besides, spectroscopic information may be stored that includes the spectral distribution of each light source and the spectral sensitivity characteristics of the imaging elements in smaller steps of wavelength. In such a case, integration in the direction of wavelength for conversion to an RGB value is performed to calculate an RGB value. Besides, the spectroscopic information about each light source and that about the imaging elements stored separately may be combined by operation.

Information about the sensitivity characteristics of imaging unit 130 of each light source for each color is acquired by normalizing an RGB value obtained by directly capturing each light source by imaging unit 130; however, any method may be used. Normalization is performed as described above, but acquiring an RGB value is not limited to this method; may be acquired from the spectral sensitivity characteristics of imaging unit 130 for each color. In such a case, the following operation may be performed. That is, the spectral sensitivity characteristics of imaging unit 130 at a wavelength to be used or multiple wavelengths including the wavelength to be used is acquired in advance, and an RGB value is acquired based on this spectral sensitivity characteristics. For example, the spectral sensitivity characteristics of imaging unit 130, obtained by sampling the range of wavelengths between 400 nm and 700 nm in 5-nm steps is stored in memory 140 in advance, and an RGB value is acquired from the spectral sensitivity characteristics of imaging unit 130 according to wavelength of a light source to be used.

The characteristics shown in FIG. 3 are the spectral sensitivity characteristics of imaging unit 130; besides FIG. 3, an imaging unit that has any spectral sensitivity characteristics may be used as long as information about the sensitivity characteristics of imaging unit 130 for each color is linearly independent. However, to increase the flexibility in choosing wavelength, an imaging unit is suitable that has a region where the colors overlap with one another as shown in FIG. 3 and a feature in which information about the sensitivity characteristics of imaging unit 130 for each color at each wavelength is linearly independent from one another in a wide range.

Besides, a discriminating unit may be newly provided that determines whether information about the sensitivity characteristics of imaging unit 130 of each light source for each color is linearly independent from one another. The discriminating unit determines whether information about the sensitivity characteristics of imaging unit 130 of each light source for each color to be used, acquired from memory 140 before operating unit 150 performs operation, is linearly independent, and passes the result to CPU 110. If CPU 110 receives a result of being linearly independent, operating unit 150 performs operation. If CPU 110 receives a result of not being linearly independent, operating unit 150 does not perform operation and informs the user by any manner that separation by operation cannot be performed with the combination of light sources to be used.

Lighting unit 120 has three light sources; besides, it may have the following configuration. That is, lighting unit 120 has any number (two or more) of light sources with different wavelengths and uses simultaneously any number of, but at most the number of colors the camera can acquire, any light sources to irradiate illumination light. In such a case, information about the sensitivity characteristics of imaging unit 130 of light sources for each color to be possibly used is stored in memory 140. For example, lighting unit 120 has light sources 121, 122, and 123, and three more light sources. The following configuration may be used. That is, in imaging under one condition, light sources 121 and 123 and one of the above three light sources are used. Under another condition, the above three light sources are used (light sources to be used are changed). Under still another condition, a different combination of light sources is used. After all, any combination of light sources may be used as long as it is changeable.

If each light-source intensities is known, the intensity of a reflected light image corresponding to the wavelength of each light source calculated by operating unit 150 may be corrected using the light-source intensity. This correction is performed by operating unit 150. For example, if the ratio of the light-source intensities of light sources 121, 122, and 123 is 1:2:3, operating unit 150 corrects the respective intensities of a reflected light image corresponding to the wavelength of each light source temporarily calculated by operating unit 150 by further multiplying them by 1, ½, and ⅓ times. This allows the ratio of the light-source intensity of each light source to be regarded as 1:1:1. Response of each wavelength can be acquired for the same light-source intensity, and thus information about the relative spectral reflectance of photographic subject 190 can be acquired. If the luminous intensity at the position of photographic subject 190 is known, information about the absolute spectral reflectance of photographic subject 190 can be acquired.

Lighting unit 120 may have a feature in which the ratio of illumination light from each light source, irradiating photographic subject 190 is spatially constant. This allows each position of photographic subject 190 to be equally evaluated when the ratio of each reflected light is calculated for analysis at each position of photographic subject 190. Meanwhile, if the ratio of illumination light from each light source, irradiating photographic subject 190 is not spatially constant, the intensity itself of illumination light is different depending on the position. Accordingly, the ratio of each reflected light by position cannot be equally evaluated. Besides, even if the ratio of illumination light from each light source, irradiating photographic subject 190 is not spatially constant, it is only required that the intensity of illumination light in the three-dimensional space is acquired for each light source in advance. In this case, if the distance to photographic subject 190 is acquired simultaneously when imaging, the three-dimensional difference in the intensity of illumination light of each light source can be corrected later.

A combination of different single-wavelength images is exemplified as single-wavelength images provided from selecting unit 160 to detecting unit 170 and determination unit 180; besides, a combination of the same single-wavelength images may be used. Any combination of single-wavelength images may be provided to detecting unit 170 and determination unit 180. Further, selecting unit 160 may change multiple single-wavelength images to be selected according to photographic subject 190.

In the description of the operation of detecting unit 170 according to the first embodiment, pixel values corresponding to the same positions of single-wavelength images containing only reflected light R2 and R3 are used to calculate the ratio for each pixel; however, a combination of single-wavelength images to be used and an operation method (e.g., difference, normalization difference) can be freely chosen. It is only necessary to use an appropriate combination of single-wavelength images and an operation method according to the photographic subject. The above-described points are the same as those in the operation of determination unit 180.

In the description of the operation of determination unit 180 according to the first embodiment, a bruise of a tomato is detected by an edge of the image, where any method can be used to detect an edge of the image. Examples of such methods include first derivation (e.g., Cany edge detection, Sobel filter) and second derivation (e.g., Laplacian filter). Besides, any process method may be used as long as it detects an edge in an image.

In the description of the operation of determination unit 180 according to the first embodiment, a bruise of a tomato is detected by an edge of the image, but a method other than edge detection may be used. For example, in the same way as the operation of detecting unit 170, the difference in spectral distributions of between the fruit and the bruise of a tomato is used, and a binary image can be generated that is produced by separating the fruit from the bruise in binary. Further, the fruit region of the binary image provided from detecting unit 170 is used as a mask image, and their logical AND is calculated to allow only a bruise present in the fruit to be extracted.

In the description of the operation of detecting unit 170 according to the second embodiment, a support vector machine is used to determine a discrimination boundary from the result of classifying the fruit and stem of a tomato; besides, other discrimination boundary determination methods (e.g., Fisher's linear discriminant analysis) may be used, or a discrimination boundary may be determined manually. A discrimination boundary may be a nonlinear function as well as a linear function. Further, a space used for determining a discrimination boundary is not limited to a plane, but may be any multidimensional space. Besides, the following method may be used. That is, a machine learning algorithm (e.g., k-nearest neighbor algorithm, deep learning) is used to classify the fruit and stem of a tomato, and a binary image is generated that is produced by separating between the fruit and bruise in binary. In the second embodiment, the description is made of binary classification of the fruit and stem of a tomato. Besides, the following operation can be performed. That is, multiple discrimination boundaries are prepared to detect three or more areas (e.g., a ripe part of the fruit, an unripe part, and the stem).

In the first through fourth embodiments, the description is made of the operation of an appearance inspection apparatus with a tomato as an example of photographic subject 190, but the disclosure is applicable to other cases. Appearance inspection apparatuses 100, 700, and 900 are widely applicable to fruit and vegetables (e.g., orange, apple), and extensively for detecting soil, damage, or rot, of food. Besides, the apparatuses are applicable for detecting an abnormal area (e.g., rust or corrosion of a structure such as an iron bridge, steel tower, and building) having spectral distributions different from that of a normal area. The apparatuses are also applicable for detecting an abnormal area (e.g., a cell part discolored due to disease, a blemish on the skin) of a living body. Generally, the same advantage is available by choosing a light-source wavelength appropriate for detecting a specific area of photographic subject 190 and for extracting its characteristic part from spectral distributions of photographic subject 190.

The description is made with the color filter arrangement of an imaging element included in imaging unit 130 according to the first embodiment being a Bayer arrangement; besides, the same advantage is available from the other arrangement such as a stripe. The arrangement of pixels of an imaging element is not limited to a checkered pattern, but other arrangements (e.g., honeycomb) may be used. Further, an example of the spectral sensitivity characteristics of a color filter disposed on each pixel of an imaging element is shown in FIG. 3; however, any filter provides the same advantage as long as it has the characteristics shown in the first embodiment even the profile of the characteristics is different.

The description is made of the configuration that detects a specific area, further extracts a more characteristic part, and displays information using single-wavelength images. Besides, a configuration may be used that informs an operator of information known from the result of extracting a characteristic part for example using a device such as an indicator other than a display device such as an LCD monitor, and a device such as a sound alarm.

The description is made of the configuration in which lighting unit 120, operating unit 150, selecting unit 160, detecting unit 170, and determination unit 180 or 780 are independent of CPU 110, 710 or 910, but other configurations such as the following configuration may be used. That is, all or part of the functions of operating unit 150, selecting unit 160, detecting unit 170, and determination units 180 and 780 are integrated into CPU 110, 710, or 910, and such functions are implemented by software programs executed on the CPU. The control function of light sources 121 through 123 by lighting unit 120 may be integrated into CPU 110, 710, or 910.

Selecting unit 160 selects single-wavelength images provided to detecting units 170 and 180; besides, CPU 110 may do it, or detecting unit 170 and determination unit 180 in themselves may do it.

CPU 910 is a control unit that controls the intensity of at least one of the multiple light sources. Instead, lighting unit 120, having a control function, may function as the above-described control unit.

In an appearance inspection apparatus of the present disclosure, each functional component (functional block) may be individually integrated into a one-chip semiconductor device such as an integrated circuit (IC) or a large-scale integration (LSI). Alternatively, one-chip integration may be performed so as to include part or all of the components. A method of circuit integration is not limited to an LSI, but may be implemented by a dedicated circuit or general-purpose processor. A field programmable gate array (FPGA), which can be programmed after the LSI is produced, or a reconfigurable processor, in which connection and setting of circuit cells inside the LSI is reconfigurable, may be used. Further, if a new technology of circuit integration appears that displaces an LSI owing to the advance of the semiconductor technology or other derivative technologies, functional blocks may be integrated using the new technology. One of such possible technologies can be biotechnology.

All or part of the above-described processes (e.g., the procedure shown in FIG. 4) may be implemented either by hardware (e.g., an electronic circuit) or by software. Further, they may be implemented by a mixture of software and hardware. Processing by software is implemented by a processor included in the appearance inspection apparatus executing control programs stored in the memory. Additionally, to implement each process in the above-described embodiments by software, part or all of the processes may be performed by separate hardware devices. For example, part of the processes may be executed at a server through a network.

The above-described embodiments are for exemplification of the technologies in the disclosure. Hence, the embodiments may undergo various kinds of change, substitution, addition, and/or omission within the scope of the claims and their equivalent technology.

INDUSTRIAL APPLICABILITY

The present disclosure is applicable to a apparatus that detects information about a specific area using the difference in the spectral distribution for each area of a photographic subject. Concrete examples of such an apparatus include a fruit sorting apparatus, endoscope, analysis apparatus, and appearance inspection apparatus.

What is claimed is:
1. An appearance inspection apparatus comprising:
  a lighting unit having a plurality of light sources emitting single-wavelength light with relative spectral distributions different from one another, the lighting unit substantially simultaneously irradiating a photographic subject with illumination light emitted by the plurality of light sources;
  an imaging unit capturing light discharged by the photographic subject in response to the illumination light irradiated by the plurality of light sources;
  a memory storing information about sensitivity characteristics of the imaging unit for each color;
  an operating unit separating an image captured by the imaging unit into a plurality of single-wavelength images including a first image, a second image, and a third image, for each component of the single-wavelength light, using the information about the sensitivity characteristics of the imaging unit for each color;

a detecting unit detecting information about a specific area of the photographic subject using the first image and the second image chosen from the plurality of single-wavelength images; and a determination unit extracting an amount of image characteristics corresponding to a characteristic part present in the specific area detected by the detecting unit using the first image and the third image chosen from the plurality of single-wavelength images.

2. The appearance inspection apparatus of claim 1,
wherein the detecting unit
calculates, for each pixel, a ratio of pixel values of the first image and the second image for a same position,
generates an image with the ratio calculated as a pixel value at an original position of a pixel,
binarizes the value for each pixel of the image generated using a predetermind threshold, and
generates a binary image having the specific area and an area other than the specific area, and
wherein the determination unit
calculates, for each pixel, a ratio of pixel values of the first image and the third image for a same position,
generates a candidate feature image with the ratio calculated as a pixel value at an original position of a pixel, and
extracts a characteristic part present in the specific area from the candidate feature image with the specific area of the binary image being a mask image.

3. The appearance inspection apparatus of claim 1,
wherein the first image is an image captured at wavelength with a largest difference of reflected-light intensities on between the specific area and an area other than the specific area, and
wherein the second image is an image captured at wavelength at which relationship of reflected-light intensities on the specific area and the area other than the specific area in the first image is reversed.

4. The appearance inspection apparatus of claim 1,
wherein the first image is an image captured in response to reflected light from the photographic subject at a wavelength of around 650 nm,
wherein the second image is an image captured in response to reflected light from the photographic subject at a wavelength of around 550 nm, and
wherein the third image is an image captured in response to reflected light from the photographic subject at a wavelength of around 450 nm.

5. The appearance inspection apparatus of claim 1,
wherein the photographic subject is a tomato,
wherein the specific area is a fruit of the tomato, and
wherein the characteristic part is a bruise on a surface of the fruit of the tomato.

6. The appearance inspection apparatus of claim 1, wherein an intensity of each of the plurality of light sources is independently controllable.

7. The appearance inspection apparatus of claim 6, further comprising a control unit controlling an intensity of at least one of the plurality of light sources,
wherein the control unit increases an intensity of a light source with a relatively low intensity of reflected light from the photographic subject, of the plurality of light sources, or decreases an intensity of a light source with a relatively high intensity of reflected light from the photographic subject, of the plurality of light sources.

8. The appearance inspection apparatus of claim 6, wherein the operating unit corrects intensities of the plurality of single-wavelength images produced by separating by operation using information about an intensity of each of the plurality of light sources.

9. The appearance inspection apparatus of claim 6, further comprising a decision unit deciding an intensity of each of the plurality of light sources, wherein the decision unit decides an intensity of each of the plurality of light sources for next imaging based on the plurality of single-wavelength images produced by separating by advance imaging.

10. The appearance inspection apparatus of claim 6, further comprising a user interface capable of receiving input of a set intensity of each of the plurality of light sources.

11. The appearance inspection apparatus of claim 1, wherein the determination unit extracts the amount of image characteristics by edge detection.

12. The appearance inspection apparatus of claim 1, further comprising an output unit outputting information about a result of extracting by the determination unit.

13. The appearance inspection apparatus of claim 1, wherein the detecting unit detects information about the specific area of the photographic subject using a discrimination boundary determined by machine learning based on one or more of chosen from the plurality of single-wavelength images.

14. The appearance inspection apparatus of claim 1, wherein the operating unit changes one or more of chosen from the plurality of single-wavelength images according to the photographic subject.

15. The appearance inspection apparatus of claim 1, further comprising an output unit outputting information about a result of detecting by the detecting unit.

16. An appearance inspection method comprising:
irradiating substantially simultaneously a photographic subject with illumination light emitted by a plurality of light sources emitting single-wavelength light with relative spectral distributions different from one another;
generating an image by capturing light discharged by the photographic subject in response to the illumination light irradiated from the plurality of light sources, by an imaging unit;
separating the image captured into a plurality of single-wavelength images including a first image, a second image, and a third image for each component of the single wavelength using the information about sensitivity characteristics of the imaging unit for each color;
detecting information about a specific area of the photographic subject using the first image and the second image chosen from the plurality of single-wavelength images; and
extracting an amount of image characteristics corresponding to a characteristic part present in the specific area detected using the first image and the third image chosen from the plurality of single-wavelength images.

* * * * *